(12) United States Patent
Sickles

(10) Patent No.: US 8,016,780 B1
(45) Date of Patent: Sep. 13, 2011

(54) ORTHOPEDIC BRACE

(76) Inventor: George Sickles, Louisville, KY (US)

( * ) Notice: Subject to any disclaimer, the term of this patent is extended or adjusted under 35 U.S.C. 154(b) by 258 days.

(21) Appl. No.: 12/348,153

(22) Filed: Jan. 2, 2009

(51) Int. Cl.
*A61F 5/00* (2006.01)

(52) U.S. Cl. .................................. 602/20; 602/4; 602/5

(58) Field of Classification Search .................. 602/4–6, 602/12–16, 19; 128/874–876, 878–881; 5/646–647
See application file for complete search history.

(56) References Cited

U.S. PATENT DOCUMENTS

| | | | | |
|---|---|---|---|---|
| 1,257,297 A * | 2/1918 | Brown | | 602/16 |
| 3,631,542 A * | 1/1972 | Potter | | 623/25 |
| 5,060,638 A | 10/1991 | Bodine, Jr. | | |
| 5,329,941 A | 7/1994 | Bodine, Jr. | | |
| 5,385,536 A | 1/1995 | Burkhead et al. | | |
| 5,665,058 A | 9/1997 | Young | | |
| 6,659,971 B2 * | 12/2003 | Gaylord | | 602/4 |
| 6,932,781 B2 | 8/2005 | Itoi | | |
| D514,224 S | 1/2006 | Fried | | |
| 7,189,213 B1 | 3/2007 | Weber | | |
| 7,244,239 B2 * | 7/2007 | Howard | | 602/4 |
| 7,300,410 B1 | 11/2007 | Weber | | |
| D561,902 S | 2/2008 | Fried | | |
| 2005/0010147 A1 | 1/2005 | Kazmierezak et al. | | |
| 2008/0228116 A1 | 9/2008 | Walker | | |

* cited by examiner

*Primary Examiner* — Michael A. Brown
(74) *Attorney, Agent, or Firm* — Robert Theuerkauf; James E. Cole; Middleton Reutlinger

(57) ABSTRACT

An orthopedic brace is provided that provides for immobilization of an injured or postoperative extremity in an abduction position and also allows the user to control internal and external rotation of the extremity. A brace is provided with two opposing members, one opposing member having a torso resting surface and the other opposing member having a forearm support surface, and an adjustment mechanism that allows a user to expand or contract the orthopedic brace to provide for internal and/or external rotation of a humeral head of the user through the forearm of the user.

29 Claims, 4 Drawing Sheets

ORTHOPEDIC BRACE

CROSS REFERENCES TO RELATED APPLICATIONS

None.

STATEMENT REGARDING FEDERALLY SPONSORED RESEARCH OR DEVELOPMENT

None.

REFERENCE TO SEQUENTIAL LISTING, ETC

None.

BACKGROUND

1. Field of the Invention

The present invention relates generally to an orthopedic brace to aid the healing of an upper extremity of an injured or postoperative patient and more specifically to a brace that can be used for total immobilization but that also provides for abduction and is adjustable to allow for internal and external rotation of the extremity.

2. Description of the Related Art

Braces and slings are used in the medical field to provide stability, support and immobilization of an upper extremity, such as an arm, which aids the healing process of an injured or postoperative extremity. However, the use of braces and slings can also cause problems during the healing process. For example, due to the immobilization of the extremity by the brace and sling patients often face problems including decreased active and passive range of motion and pain that may lead to conditions such as "frozen shoulder." Such problems can hinder the patient's recovery and their ability to return to daily activities.

Traditional braces and slings immobilize an injured extremity by holding the extremity close to the patient's torso with the elbow flexed at approximately 90 degrees. However, the complete lack of movement of the extremity can cause over time the problems discussed above. As a result, and in order to alleviate such problems, patients often times must undergo physical therapy, such as abduction and internal and external rotation of the extremity. Abduction is generally movement of the upper arm away from the lateral border of the torso. External rotation is generally movement of the humeral head in the transverse plane away from the torso through the forearm flexed at approximately 90 degrees. And, internal rotation is generally movement of the humeral head in the transverse plane toward the torso through the forearm flexed at approximately 90 degrees. For purposes of further description of the above movements, the transverse plane as used above is a horizontal plane passing through a standing human body so that the transverse plane is parallel to the floor or perpendicular to the long axis of the human body. Further, the humeral head as used above is the hemispherical head of an upper arm of a human body which articulates with the glenoid fossa or cavity of the scapula.

Typical braces and slings do not allow for abduction and internal or external movement of an extremity as discussed above. Moreover, many braces and/or slings that allow for abduction do not allow for external or internal rotation. However, even those braces that allow for abduction and internal and external rotation typically contain complex structures including multiple bolts, guide rails and/or support posts, or require multiple braces. Consequently, such braces and slings are bulky, heavy, not easily adjusted (i.e., requiring another person to aid the patient in setting up and adjusting the brace and sling) and costly to manufacture.

Thus, there is a need for a simple, light weight and cost effective orthopedic brace that can be used with a sling to immobilize an upper extremity but to also allow movement (i.e., abduction and internal and external rotation) of the extremity while still providing stability and support. Such a brace will not only provide the necessary support and immobilization to promote healing but will also allow the patient the ability to move the extremity as instructed by their healthcare professional to help prevent the common problems associated with immobilization. As a result, such problems associated with the immobilization of an extremity can be relieved or reduced by a patient's use of such a brace in conjunction with other physical therapy directed by a healthcare professional.

SUMMARY OF THE INVENTION

Some embodiments of the invention provide a brace that provides for abduction of a patient's extremity and also provides for internal and external rotation of the extremity.

Some embodiments of the invention provide a brace that provides an adjustment mechanism that allows the user to control the internal and external rotation of the user's extremity.

Some embodiments of the invention provide a brace having a first member and a second member, one of the first and second members having a first anterior end, a first posterior end and a torso resting surface, and the other of the first and second members having a second anterior end, a second posterior end and a forearm support surface, the first and second members being moveably connected at one of the first and second posterior ends or the first and second anterior ends, and an adjustment mechanism movably coupling the first and second members, the adjustment mechanism capable of causing said torso resting surface and said forearm support surface to converge and diverge.

Some embodiments of the invention provide a brace having a first elongated member and a second elongated member, the first elongated member having a first posterior end, a first anterior end and a torso resting surface, with the torso resting surface connecting the first posterior end and first anterior end, the second elongated member having a second posterior end, a second anterior end and a forearm support surface, with the forearm support surface connecting the second posterior end and the second anterior end, the first elongated member and the second elongated member being moveably attached at one of the first and second posterior ends or the first and second anterior ends, and an adjustment mechanism movably coupling the first elongated member and the second elongated member, the adjustment mechanism capable of rotating the second elongated member between at least a first position and a second position.

Some embodiments of the invention provide a brace having a first opposing member and a second opposing member, one of the first and second opposing members having a torso resting surface and the other of the first and second opposing members having a forearm support surface, the first and second opposing members being hingeably connected at one end, and an adjustment mechanism capable of rotating the forearm support surface between at least a first position and a second position, the forearm support surface being closer to said torso resting surface in said first position than in said second position.

Some embodiments of the invention provide a brace having opposing members moveably connected at one end, one opposing member having a torso resting surface, the other opposing member having a forearm support surface, the brace also having an adjustment mechanism disposed between the opposing members, the adjustment mechanism having a control device allowing for movement of the adjustment mechanism and therefore movement of the opposing members to provide internal and external rotation of a humeral head of a user through the forearm of the user. The control device being either a manually operated knob or a battery-operated motor for continuous passive motion.

Some embodiments of the invention provide a brace capable of cooperating with a sling to provide stability and support to an upper extremity. The brace having two members moveably connected at one end, one member having a torso resting surface, the other member having a forearm support surface, the support also having an adjustment mechanism disposed between the members to provide for internal and external rotation of a humeral head of a user through the forearm of the user. The torso resting surface and the forearm support surface may also be covered by a pad or cushion. The brace further having a torso strap for securing the brace to the torso of a user.

Other objects and advantages will become apparent from the following description taken in connection with the accompanying drawings, wherein is set forth, by way of illustration and examples, embodiments of this invention.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

DETAILED DESCRIPTION

Figure 1:
FIG. 1 is a perspective view of an exemplary brace.

It is to be understood that the invention is not limited in its application to the details of construction and the arrangement of components set forth in the following description or illustrated in the drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "attached," "coupled," and "mounted," and variations thereof herein are used broadly and encompass direct and indirect connections, attachments, couplings, and mountings. In addition, the terms "connected" and "coupled" and variations thereof are not restricted to physical or mechanical connections or couplings.

Furthermore, and as described in subsequent paragraphs, the specific mechanical configurations illustrated in the drawings are intended to exemplify embodiments of the invention and that other alternative mechanical configurations are possible.

Referring now in detail to the drawings, wherein like numerals indicate like elements throughout the several views, there are shown in FIGS. 1-4 various aspects of an orthopedic brace. The orthopedic brace of the present description provides a design that in cooperation with a sling provides support, stability and immobilization of an upper extremity. The orthopedic brace, however, also provides for abduction of an upper extremity and is capable of providing for internal and external rotation of the extremity. Further, the orthopedic brace of the present description allows the user to adjust the orthopedic brace and therefore control the external and internal rotation. The above is accomplished by an orthopedic brace that is light weight and user friendly.

Referring to FIG. 1, one embodiment of an orthopedic brace 10 is shown. The brace 10 is shown being used in conjunction with a sling 40 to provide stability and support to an upper extremity of a user 50. The upper extremity of user 50 is held in a sling 40 as shown.

Figure 2:
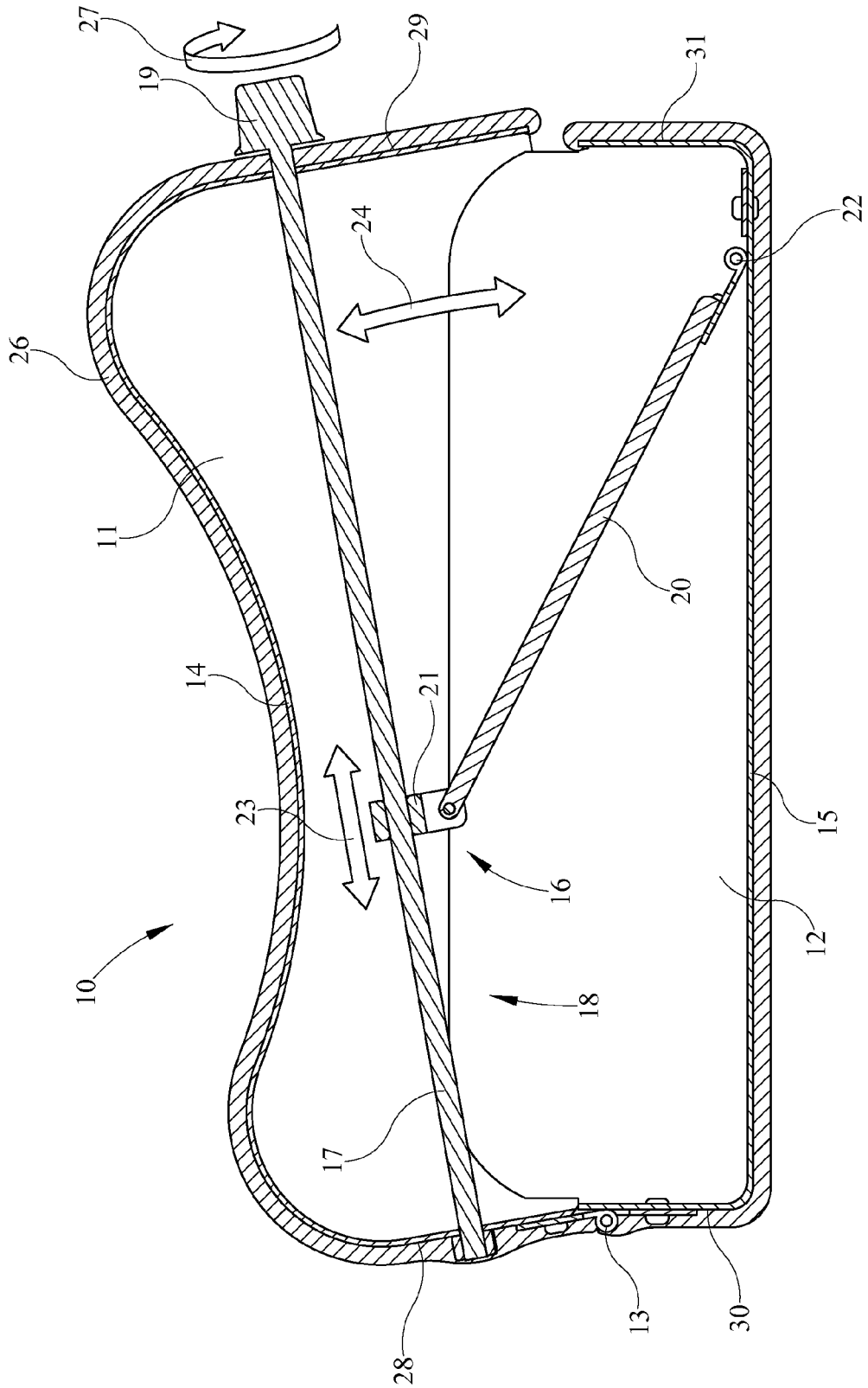
FIG. 2 is a cross-sectional view of an embodiment of a brace.
Figure 3:
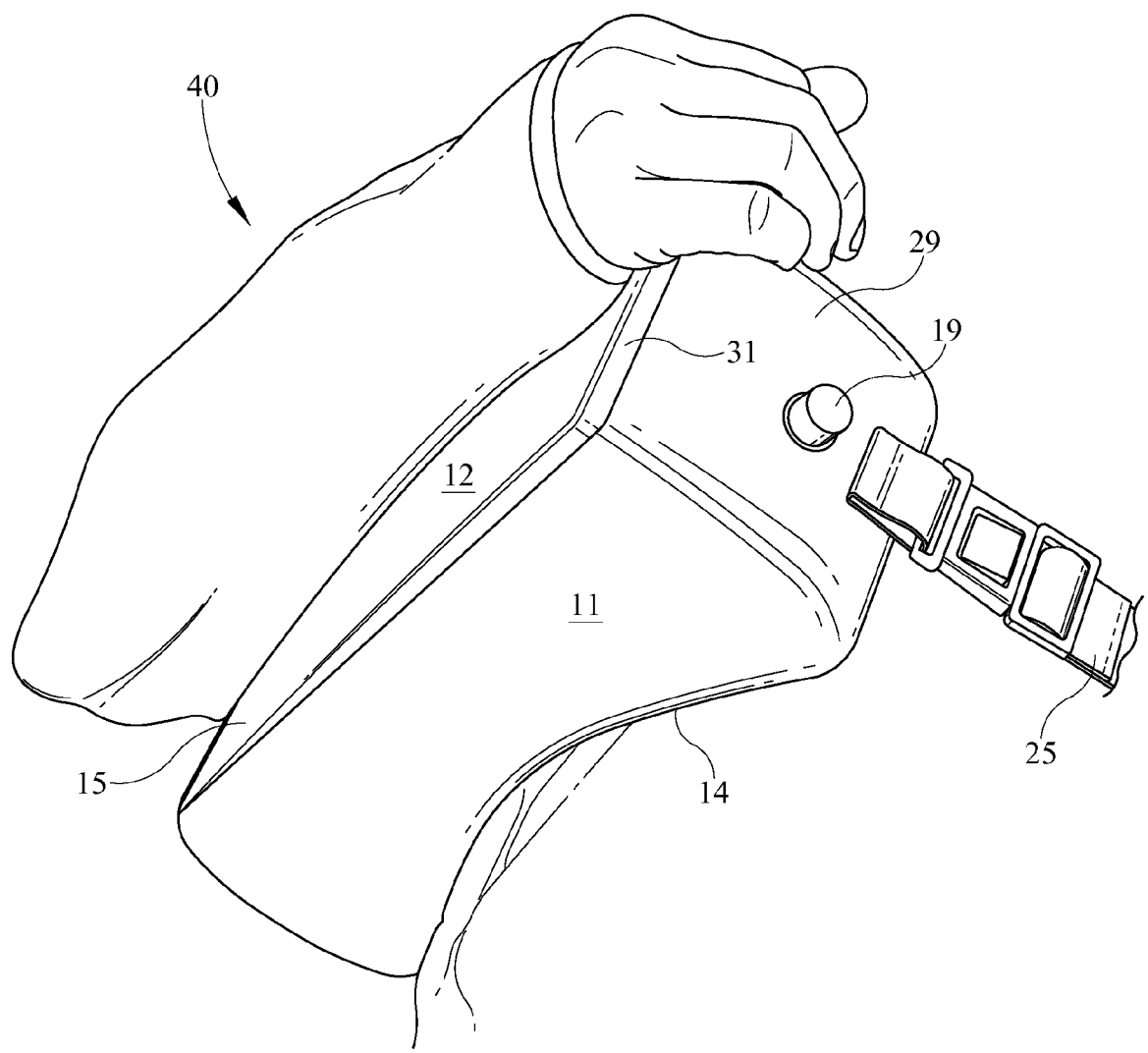
FIG. 3 is a perspective view of an exemplary brace.

As can be seen in FIG. 2, the brace 10 has two opposing members 11 and 12 that are movably connected at one end by a hinge 13. However, one skilled in the art will realize that members 11 and 12 do not have to be connected by a hinge, but can be connected by any method, such as by a flex connection, to allow for members 11 and 12 to move relative to each other. Further, members 11 and 12 may be made of molded plastic. However, one skilled in the art will realize that other materials may be substituted herein and are well within the scope of the present invention. Members 11 and 12 also provide for an open or hollow area 18 when connected. Moreover, in the embodiment shown herein and as best seen in FIG. 3, members 11 and 12 can be of different sizes so that one member is capable of sliding or fitting inside the other member.

As further seen in the exemplary embodiment, member 11 has a posterior end 28, anterior end 29, and a torso resting surface 14 which connects posterior end 28 and anterior end 29. Further, in the embodiment shown, torso resting surface 14 is contoured to better fit against the torso of the user 50 and, as seen in FIG. 1, is a substantially vertical surface when user 50 is in a standing position utilizing brace 10. Member 12 has a posterior end 30, anterior end 31, and a forearm support surface 15 which connects posterior end 30 and anterior end 31. In the embodiment shown, forearm support surface 15 is substantially flat to support the forearm of user 50 and, as seen in FIG. 1, is also a substantially vertical surface when user 50 is in a standing position utilizing brace 10. Torso resting surface 14 and forearm support surface 15 may be covered by a cushioned material 26 to provide added comfort for the user 50. Brace 10 can also utilize torso strap 25 to keep brace 10, and particularly torso resting surface 14, in position against the torso of user 50.

Members 11 and 12 are movably coupled by an adjustment mechanism 16. Adjustment mechanism 16 of one embodiment has a threaded rod 17 disposed in open area 18. Threaded rod 17 extends the length of member 11. One end of threaded rod 17 is rotatably connected to the inside of member 11 with the other end of threaded rod 17 extending to the outside of member 11 with a control knob 19 connected thereto. Adjustment mechanism 16 further has a pivot rod or strut 20 disposed within the brace 10 with one end hingeably connected by a hinge 22 to the inside of member 12 and the other end hingeably connected to a threaded nut 21. Threaded nut 21 is connected or threaded to threaded rod 17. Again, however, one skilled in the art will realize that other connections, such as flex connections, may be utilized rather than utilizing hinges as described in this embodiment. Further, adjustment mechanism 16 may be made of metal. However, one skilled in the art will realize that other materials, such as plastic, may be substituted herein and are well within the scope of the present invention.

Further, those skilled in the art will realize that threaded rod 17, threaded nut 21 and pivot rod or strut 20 can be of different sizes and/or diameters, which will necessarily change the sensitivity of adjustment mechanism 16. A larger diameter threaded rod 17, and therefore a larger diameter threaded nut 21, will provide for greater movement between members 11 and 12 when control knob 19 is turned a full rotation, for example, as compared to an adjustment mechanism 16 with a smaller diameter threaded rod 17 and threaded nut 21.

In operation, control knob 19 can be turned either clockwise or counterclockwise thereby turning threaded rod 17 in either a clockwise or counterclockwise direction. The turning of threaded rod 17 causes threaded nut 21 to move along the length of threaded rod 17 as indicated by arrow 23. As control knob 19 is turned in a clockwise direction, for example, as indicated by arrow 27, threaded nut 21 moves in the direction of control knob 19 and, consequently, pivot rod or strut 20 also moves in a direction toward control knob 19. In other words, pivot rod or strut 20 moves toward a position perpendicular to forearm support surface 15. This movement of threaded nut 21 and pivot rod or strut 20 causes members 11 and 12 to move away (i.e., diverge) from each other as indicated by arrow 24. Further, in use, when members 11 and 12 move away from each other, forearm support surface 15 moves away from torso resting surface 14 causing external rotation of the humeral head of the user 50 through the forearm of user 50.

As further provided in this embodiment, when control knob 19 is turned in a direction opposite than that discussed above, thereby turning threaded rod 17 in the opposite direction, threaded nut 21 and pivot rod or strut 20 move in a direction toward hinge 13. In other words, pivot rod or strut 20 moves toward a position parallel to forearm support surface 15. This movement of threaded nut 21 and pivot rod or strut 20 causes members 11 and 12 to move in a direction toward (i.e., converge) each other. Further, in use, when members 11 and 12 move toward each other, forearm support surface 15 moves toward torso resting surface 14 causing internal rotation of the forearm of user 50. Also, because adjustment mechanism 16 does not require the loosening or tightening of screws, bolts, nuts, or the like, members 11 and 12 are not free to move relative to one another unless they are being adjusted. Instead, adjustment mechanism 16 utilizes threaded rod 17 and threaded nut 21, which allows members 11 and 12 to maintain some resistance between each other while being adjusted.

Despite the ability to adjust brace 10 as discussed above, those skilled in the art will realize that adjustment may not be necessary or desirable and that the upper extremity can be immobilized by setting members 11 and 12 at a desired position and foregoing any further adjustments. Moreover, those skilled in the art further realize that the width of brace 10 provides for abduction of the user's 50 extremity when placed in position by causing the upper portion of the extremity to be placed away from the lateral border of the torso. Therefore, to provide different degrees of abduction, brace 10 can be manufactured to different widths.

Figure 4:
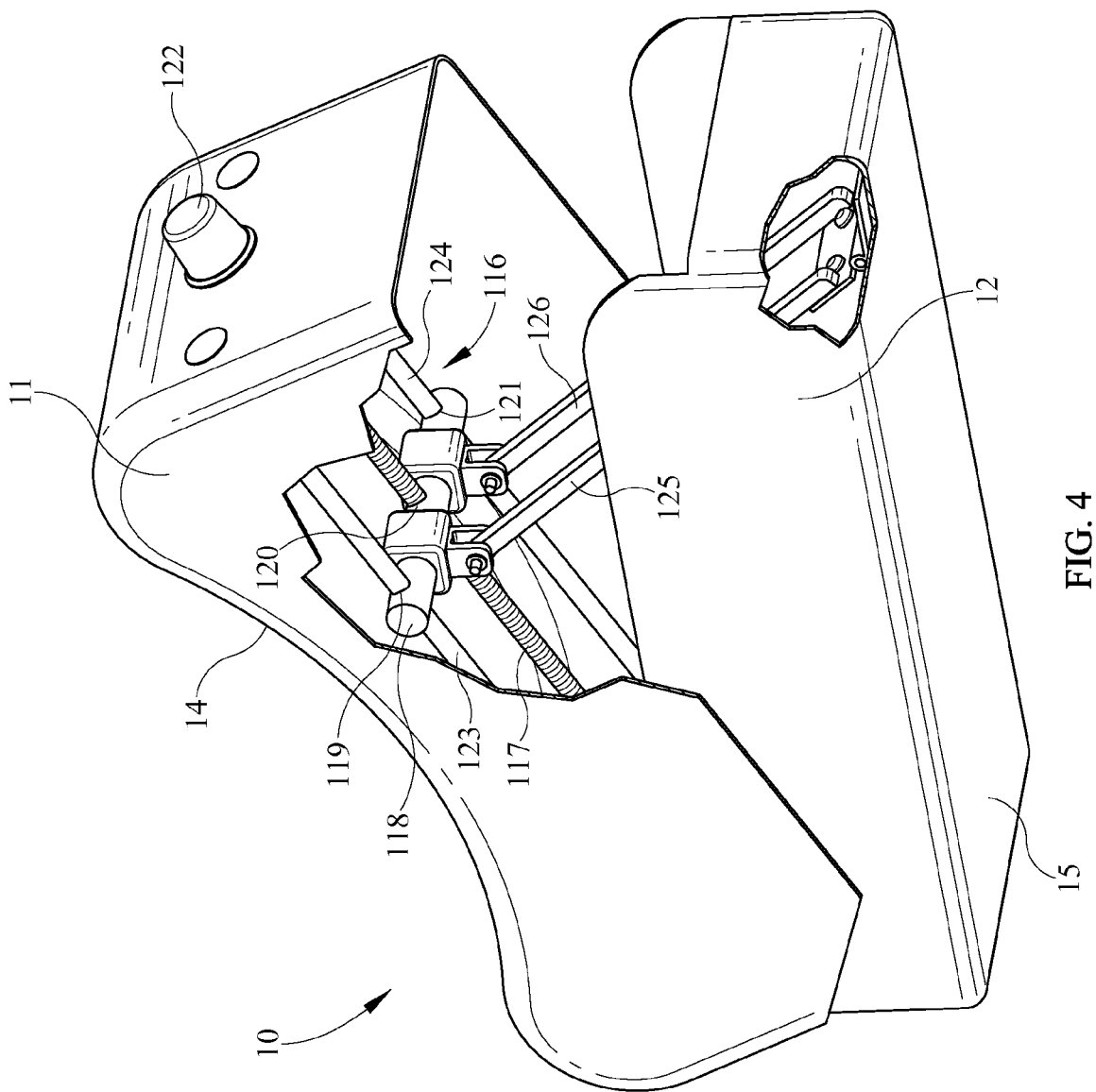
FIG. 4 is a perspective view of an alternative embodiment of the adjustment mechanism of an exemplary brace.

In FIG. 4 an alternative embodiment of the adjustment mechanism 116 is shown. This alternative embodiment of adjustment mechanism 116 as hereafter described provides for greater stability of brace 10, and particularly member 12, when members 11 and 12 are in a position extended away from each other. Adjustment mechanism 116 has a threaded rod 117 disposed in open area 18 of brace 10. Similar to the other embodiment described above, threaded rod 117 extends the length of member 11. One end of threaded rod 117 is rotatably connected to the inside of member 11 with the other end of threaded rod 117 extending to the outside of member 11 with a control knob 122 connected thereto. Adjustment mechanism 116 further has support rods 123 and 124 that are connected to member 11 and are substantially parallel to threaded rod 117. Adjustment mechanism 116 further has a support rod 118. Support rod 118 contains a threaded opening 120 and two smooth openings 119 and 121. Threaded rod 117 is threaded through threaded opening 120 and support rods 123 and 124 extend through smooth openings 119 and 121.

Adjustment mechanism 116 further has pivot rods or struts 125 and 126 that are hingeably connected to member 12 at one end and support rod 118 at the other end. In operation, control knob 122 can be turned either clockwise or counterclockwise thereby turning threaded rod 117 in either a clockwise or counterclockwise direction. The turning of the threaded rod 117 causes support rod 118 to move along the length of threaded rod 117 due to threaded opening 120. Concurrently, support rod 118 also slides along support rods 123 and 124 due to smooth openings 119 and 121. Further, as control knob 122 is turned so that support rod 118 moves in the direction of control knob 122, pivot rods or struts 125 and 126 also move in a direction toward control knob 122. This movement of support rod 118 and pivot rods or struts 125 and 126 causes members 11 and 12 to move away from each other and therefore provide for external rotation of a forearm of the user 50. Similarly, as discussed above in conjunction with adjustment mechanism 16, turning control knob 122 in the opposite direction causes the opposite effect, i.e., members 11 and 12 move toward each other and therefore provide for internal rotation of the forearm of user 50.

In a further alternative embodiment (not shown) of adjustment mechanism 16 or 116, threaded rod 17 or 117 can be rotated in a clockwise or counterclockwise direction by a battery-operated motor. In this embodiment, user 50 has access to a lever or button that can be manipulated to cause the battery-operated motor to rotate threaded rod 17 or 117 in either a clockwise or counterclockwise direction. Further, the motor and the lever or button used to control the motor can be of such a design that the motor can also provide for continuous passive motion of the injured or postoperative extremity of user 50. In other words, user 50 can press or hold the motor lever or button causing threaded rod 17 or 117 to continuously rotate in a clockwise and/or counterclockwise direction which in turn will provide continuous passive motion (i.e., continuous external and/or internal rotation) of the user's 50 extremity.

In use, for example, user 50 can attach brace 10 to his or her torso with torso strap 25 and with torso resting surface 14 resting against the torso of user 50. User 50 then can place his or her arm into sling 40 and rest his or her forearm against forearm support surface 15. Brace 10 and sling 40 in conjunction immobilize the upper extremity of user 50. With members 11 and 12 set at a desired position, the width of brace 10 provides for abduction of the upper extremity without any further adjustment. However, user 50 can manipulate control knob 19 to expand brace 10 (causing members 11 and 12 to move away from each other) or contract brace 10 (causing members 11 and 12 to move toward each other), providing for either external or internal rotation, respectively, of the extremity of user 50. As brace 10 expands, user's 50 forearm moves in the transverse plane away from user's 50 torso causing rotation of the user's 50 humeral head (i.e., external rotation). As brace 10 contracts, user's 50 forearm moves in the transverse plane toward user's 50 torso causing rotation of the user's 50 humeral head (i.e., internal rotation).

The foregoing description of structures and uses has been presented for purposes of illustration. It is not intended to be exhaustive or to limit the invention to the precise forms and/or uses disclosed, and obviously many modifications and variations are possible in light of the above teaching. For example, it will be understood by those skilled in the art that the shape, width, and height of the brace 10 can be of different sizes to better fit user 50. It is understood that while certain forms of the brace have been illustrated and described, it is not limited thereto except insofar as such limitations are included in the following claims and allowable functional equivalents thereof.

What is claimed is:

1. An orthopedic brace, comprising:
   a first member and a second member;
   one of said first and second members having a first anterior end, a first posterior end and a torso resting surface, and the other of said first and second members having a second anterior end, a second posterior end and a forearm support surface;
   said first and second members being moveably connected at one of said first and second posterior ends or said first and second anterior ends; and
   an adjustment mechanism movably coupling said first and second members, said adjustment mechanism capable of causing said torso resting surface and said forearm support surface to converge and diverge in a transverse plane.

2. The orthopedic brace of claim 1 wherein said adjustment mechanism has a control device controllable by a user for causing said torso resting surface and said forearm support surface to converge and diverge.

3. The orthopedic brace of claim 2 wherein said control device is a knob.

4. The orthopedic brace of claim 2 wherein said control device is a battery-operated motor.

5. The orthopedic brace of claim 1 wherein said forearm support surface and said torso resting surface are substantially vertical.

6. The orthopedic brace of claim 1 wherein at least one of said forearm support surface and said torso resting surface is covered by a cushioned material.

7. The orthopedic brace of claim 1 wherein at least one of said first and second members has a strap for securing said torso resting surface against a torso of a user.

8. The orthopedic brace of claim 1 wherein said torso resting surface is contoured.

9. The orthopedic brace of claim 1 wherein said adjustment mechanism provides for external rotation and internal rotation of a humeral head through a forearm of a user.

10. An orthopedic brace, comprising:
    a first elongated member and a second elongated member;
    said first elongated member having a first posterior end, a first anterior end and a torso resting surface, said torso resting surface connecting said first posterior end and said first anterior end;
    said second elongated member having a second posterior end, a second anterior end and a forearm support surface, said forearm support surface connecting said second posterior end and said second anterior end;
    said first elongated member and said second elongated member being moveably attached at one of said first and second posterior ends or said first and second anterior ends; and
    an adjustment mechanism movably coupling said first elongated member and said second elongated member, said adjustment mechanism capable of externally rotating said second elongated member through a substantially horizontal plane between at least a first position and a second position.

11. The orthopedic brace of claim 10 wherein said adjustment mechanism has a control device controllable by a user for rotating said second elongated member between at least said first and second positions.

12. The orthopedic brace of claim 11 wherein said control device is a knob.

13. The orthopedic brace of claim 11 wherein said control device is a battery-operated motor.

14. The orthopedic brace of claim 10 wherein said forearm support surface and said torso resting surface are substantially vertical.

15. The orthopedic brace of claim 10 wherein said first position is a position where said forearm support surface is closer to said torso resting surface than in said second position.

16. The orthopedic brace of claim 10 wherein at least one of said forearm support surface and said torso resting surface is covered by a cushioned material.

17. The orthopedic brace of claim 10 wherein said torso resting surface is contoured.

18. The orthopedic brace of claim 10 wherein at least one of said first and second elongated members has a strap for securing said torso resting surface against a torso of a user.

19. The orthopedic brace of claim 10 wherein said adjustment mechanism provides for external rotation and internal rotation of a humeral head through a forearm of a user.

20. An orthopedic brace, comprising:
    a first opposing member and a second opposing member;
    one of said first and second opposing members having a torso resting surface and the other of said first and second opposing members having a forearm support surface,
    said first and second opposing members being hingeably connected at one end,
    an adjustment mechanism capable of internally rotating said forearm support surface between at least a first position and a second position through a transverse plane,
    said forearm support surface being closer to said torso resting surface in said first position than in said second position.

21. The orthopedic brace of claim 20 wherein said adjustment mechanism has a control device controllable by a user for causing said forearm support surface to move between said first and second positions.

22. The orthopedic brace of claim 21 wherein said control device is a knob.

23. The orthopedic brace of claim 22 wherein said control device is a battery-operated motor.

24. The orthopedic brace of claim 20 wherein said forearm support surface and said torso resting surface are substantially vertical.

25. The orthopedic brace of claim 20 wherein at least one of said torso resting surface and said forearm support surface is covered by a cushioned material.

26. The orthopedic brace of claim 20 wherein at least one of said first and second opposing members has a strap for securing said torso resting surface against a torso of a user.

27. The orthopedic brace of claim 20 wherein said torso resting surface is contoured.

28. The orthopedic brace of claim 20 wherein said adjustment mechanism provides for external rotation and internal rotation of a humeral head through a forearm of a user.

29. An orthopedic brace, comprising:
- a first member and a second member;
- one of said first and second members having a first anterior end, a first posterior end and a torso resting surface, and the other of said first and second members having a second anterior end, a second posterior end and a forearm support surface;
- said first and second members being moveably connected at one of said first and second posterior ends or said first and second anterior ends; and
- an adjuster movably coupling said first and second members, said adjuster capable of causing said torso resting surface and said forearm support surface to converge and diverge in a transverse plane.

* * * * *